United States Patent
Arlt

(10) Patent No.: US 7,241,898 B2
(45) Date of Patent: Jul. 10, 2007

(54) METATHESIS CATALYSTS

(75) Inventor: Dieter Arlt, Lemgo (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 265 days.

(21) Appl. No.: 10/901,785

(22) Filed: Jul. 29, 2004

(65) Prior Publication Data

US 2005/0049417 A1 Mar. 3, 2005

Related U.S. Application Data

(60) Provisional application No. 60/503,013, filed on Sep. 15, 2003.

(30) Foreign Application Priority Data

Aug. 2, 2003 (DE) ................ 103 35 416

(51) Int. Cl.
C07F 15/00 (2006.01)

(52) U.S. Cl. ................ 548/101; 548/262.2; 548/300.1; 560/8

(58) Field of Classification Search ................ 548/101, 548/262.2, 300.1; 560/8
See application file for complete search history.

(56) References Cited

U.S. PATENT DOCUMENTS

| 4,654,435 A | 3/1987 | Kitahara |
| 2002/0107138 A1 | 8/2002 | Hoveyda |
| 2004/0127350 A1 | 7/2004 | Grela |

FOREIGN PATENT DOCUMENTS

| JP | 59118721 A2 | 7/1984 |
| WO | WO0214376 A2 | 2/2002 |

OTHER PUBLICATIONS

Ahmad-Junan, S. Asiah; Aryloxymethyl Radical Cyclizations Mimicking Biological C-C Bond Formation to Methoxy Groups; J. Chem. Soc. Perkin Trans 1, 1992 (pp. 2313-2320).
Wyrzykiewicz, Elzbieta; N-(E)-2-stilbenyloxymethylenecarbonyl substituted hydrazones of ortho-, meta-, and parahydroxybenzaldehydes. Bulletin of the Polish Academy of Sciences, Chemistry, vol. 48, No. 3, 2000, pp. 213-229, and Chemical Abstract 134:131292.
Tietze, Lutz, F.; Intra- and Intermolecular Hetero-Diels-Alder Reactions of Alkylidene-and Benzylidenepyrazolones and Benzylideneisoxazolones, Investigations toward the Conformation of the Transition State, J. Org. Chem. vol. 53 No. 4, 1998 (pp. 810-820).
Panarin, E. F.; Derivatives of o-vinylphenol. Synthesis of .alpha.-(o-vinylphenoxy) carboxylic acids; Chemical Abstracts 85:20772 (1973).
Newsoroff, G. P., Nuclear Magnetic resonance spectra of .alpha., .beta, beta.-trimethylstyrenes. Australian Journal of Chemistry, vol. 19 No. 9,(1966), (pp. 1667-1675) and Chemical Abstract 65:90114.
Nippon Zeon, C., Ltd., Japan; Addition reactions of unsaturated compounds; Japan Kokai Tokkyo Chemical Abstracts 102:8602 for JP 59 118721 (1984).
Wakamatsu, H., Ein hochaktiver und luftstabiler Rutheniumkomplex fur die Olefinmetathese; Agnew. Chem 2002, 114, No. 5, 832-834.
Wakamatsu, H., A New Highly Efficient Ruthenium Metathesis Catalyst; Agnew. Chem 2002, 114, No. 13, 2509-2511.
Grela, K., A Highly Efficient Ruthenium Catalyst for Methathesis Reactions; Agnew. Chem 2002, 114, No. 21, 4210-4212.
Dieter Arlt; Novel Ruthenium Catalyst; U.S. Appl. No. 11/004,113, filed Dec. 3, 2004.

Primary Examiner—Joseph K. McKane
Assistant Examiner—Rei-tsang Shiao
(74) Attorney, Agent, or Firm—Michael P. Morris; Philip I. Datlow; Mary-Ellen M. Devlin

(57) ABSTRACT

The present invention relates to new compounds of formula 1, the preparation thereof, intermediate products for preparing them and the use of the compounds of formula 1 as catalysts in various metathesis reactions

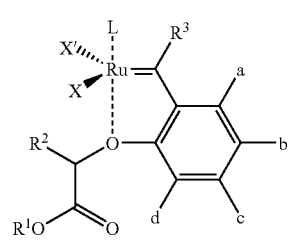

The new metathesis catalysts, which are obtained from readily accessible preliminary products, have a high activity and can be used for all kinds of metathesis reactions.

6 Claims, 1 Drawing Sheet

Umsatz [Peakflaechen%; Product/Edukt] = Conversion [Peak Area %; Product/Educt]

Zeit = Time

METATHESIS CATALYSTS

RELATED APPLICATIONS

This application claims benefit of U.S. Ser. No. 60/503,013, filed Sep. 15, 2003, which is hereby incorporated by reference in its entirety.

FIELD OF THE INVENTION

The present invention relates to new compounds of formula 1, the preparation thereof, intermediate products for preparing them and the use of the compounds of formula 1 as catalysts in various metathesis reactions

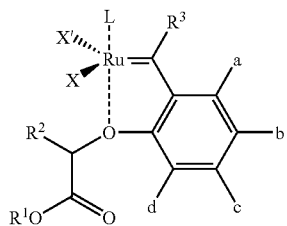

1

BACKGROUND OF THE INVENTION

Ruthenium complexes of formula A are known from WO 02/14376 A2 and are described as active, air-stable and recoverable metathesis catalysts. Catalysts of this kind which have an even greater activity than A have also become known (Angew. Chem. 2002, 114, No. 5, 832-834; Angew. Chem. 2002, 114, No. 13, 2509-2511; Angew. Chem. 2002, 114, No. 21, 4210-4212), and are described by the formulae B, C and D.

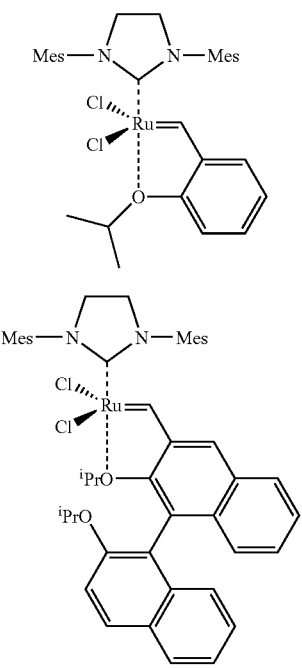

A

B

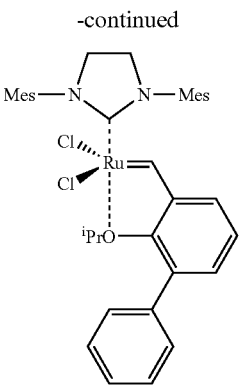

C

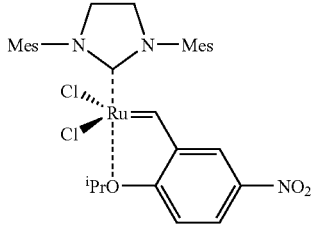

D

The improvement in the activity of B, C and D compared with A is due to steric and electronic effects of the substituents at the phenyl nucleus of the isopropoxy-phenylmethylene ligand. It has now been found, surprisingly, that a major increase in the activity of metathesis catalysts of type A can be achieved by making particular changes to the aliphatic moiety of the ether group.

DETAILED DESCRIPTION OF THE INVENTION

Figure 1:
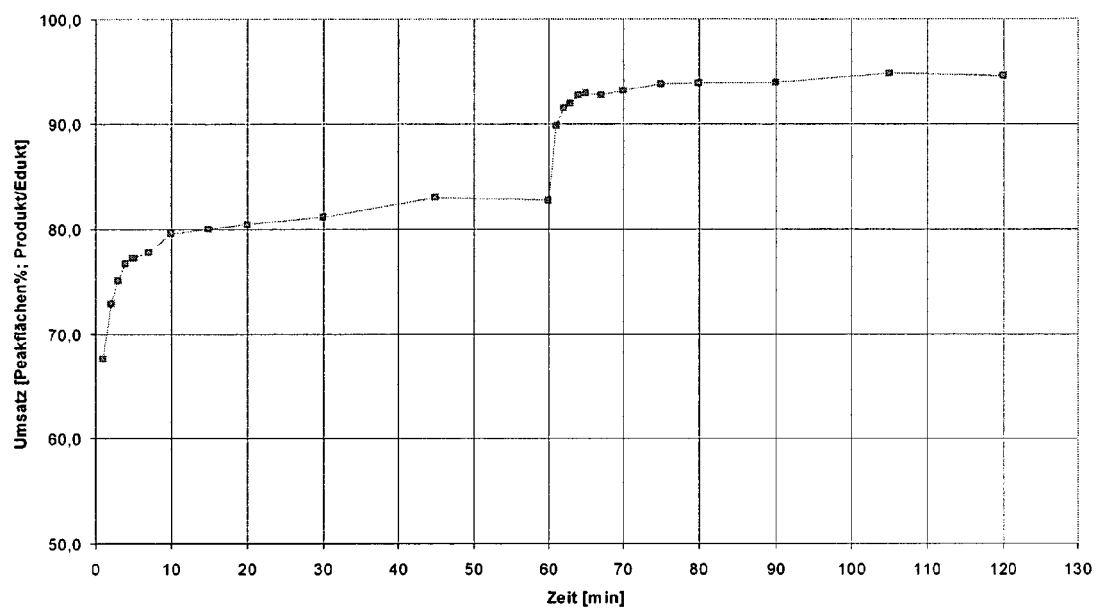
FIG. 1 shows the cyclization rate of a particular di-olefinic substrate in the presence of a metathesis catalyst according to the present invention.

The present invention relates to new ruthenium complexes of formula 1 and their use as metathesis catalysts,

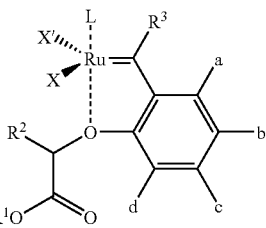

1 wherein
 X and X' denote anionic ligands; preferably halogen, particularly preferably Cl or Br;
 L denotes a neutral ligand;
 a, b, c, d independently of one another denote H, —NO$_2$, C$_{1-12}$-alkyl, C$_{1-12}$-alkoxy or phenyl, while phenyl may optionally be substituted by a group selected from among C$_{1-6}$-alkyl and C$_{1-6}$-alkoxy;

$R^1$ denotes $C_{1-12}$-alkyl, $C_{5-6}$-cycloalkyl, $C_{7-18}$-aralkyl, aryl;

$R^2$ denotes H, $C_{1-12}$-alkyl, $C_{5-6}$-cycloalkyl, $C_{7-18}$-aralkyl, aryl;

$R^3$ denotes H, $C_{1-12}$-alkyl, $C_{2-12}$-alkenyl, $C_{2-12}$-alkynyl, aryl.

Preferred compounds are the compounds of formula 1, wherein

X and X' denote halogen;

L denotes a neutral ligand;

a, b, c, d independently of one another denote H, —$NO_2$, $C_{1-6}$-alkyl, $C_{1-6}$-alkoxy or phenyl, while phenyl may optionally be substituted by a group selected from among $C_{1-4}$-alkyl and $C_{1-4}$-alkoxy;

$R^1$ denotes $C_{1-6}$-alkyl, $C_{5-6}$-cycloalkyl, $C_{7-11}$-aralkyl, aryl;

$R^2$ denotes H, $C_{1-6}$-alkyl, $C_{5-6}$-cycloalkyl, $C_{7-11}$-aralkyl, aryl;

$R^3$ denotes H, $C_{1-6}$-alkyl, $C_{2-6}$-alkenyl, $C_{2-6}$-alkynyl, aryl;

particularly preferred compounds being the compounds of formula 1 wherein

X and X' denotes Cl or Br;

L denotes a neutral ligand;

a, b, c, d independently of one another denote H, —$NO_2$, methyl, ethyl, iso-propyl, methoxy, or phenyl, while phenyl may optionally be substituted by a group selected from among methyl and methoxy;

$R^1$ denotes methyl, ethyl, n-propyl, iso-propyl, n-butyl, sec-butyl, tert-butyl, n-heptyl, cyclopentyl, cyclohexyl, 2-methylcyclohexyl, 2,4-dimethylcyclohexyl benzyl, 1-phenylethyl, 2-phenylethyl, phenyl, o-, m-, p-tolyl and 3,5-dimethylphenyl.

$R^2$ denotes H, methyl, ethyl, n-propyl, iso-propyl, n-butyl, sec-butyl, tert-butyl, n-heptyl, cyclopentyl, cyclohexyl, 2-methylcyclohexyl, 2,4-dimethylcyclohexyl benzyl, 1-phenylethyl, 2-phenylethyl, phenyl, o-, m-, p-tolyl and 3,5-dimethylphenyl.

$R^3$ denotes H, methyl, ethyl, phenyl.

Particularly preferred compounds among the above-mentioned compounds of general formula 1 are those wherein $R^1$, $R^2$, $R^3$, X, X' and L may have the meanings specified and a, b, c denote H; and d denotes phenyl which may be substituted by a group selected from among $C_{1-6}$-alkyl and $C_{1-6}$-alkoxy;

or a, c, d denote H; and b denotes —$NO_2$.

Also particularly preferred among the above-mentioned compounds of general formula 1 are those wherein $R^1$, $R^2$, $R^3$, X, X', a, b, c and d may have the meanings specified and L denotes $P(R^4)_3$ or a ligand of formula $L^1$, $L^2$, $L^3$ or $L^4$, wherein

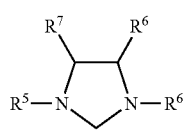

$L^1$

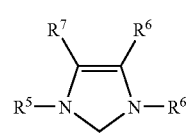

$L^2$

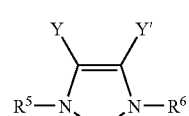

$L^3$

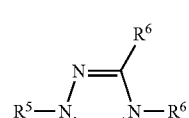

$L^4$ $R^4$ denotes $C_{1-6}$-alkyl, cycloalkyl or aryl $R^5$ and $R^6$ independently of one another denote H, $C_{1-6}$-alkyl or aryl;

$R^7$ and $R^8$ independently of one another denote H, $C_{1-6}$-alkyl, $C_{2-6}$-alkenyl or aryl; or $R^7$ and $R^8$ together form a 3- or 4-membered alkylene bridge; and Y and Y' denote halogen; preferably Cl or Br.

Most preferred are compounds of general formula 1, wherein

X and X' denote Cl;

L denotes $L^1$;

a, b, c, d denote H;

$R^1$ denotes methyl;

$R^2$ denotes methyl;

$R^3$ denotes H;

$R^5$ and $R^6$ denote mesityl;

$R^7$ and $R^8$ denote H.

The new compounds of formula 1 are obtained by reacting preligands of formula 2 with ruthenium complexes of formula 3

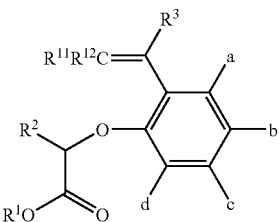

2

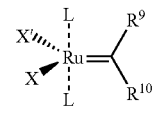

3 where $R^3$, a, b, c and d have the meanings given for formula 1 and $R^1$ denotes $C_{1-12}$-alkyl, $C_{5-6}$-cycloalkyl, $C_{7-18}$-aralkyl, aryl; preferably $C_{1-6}$-alkyl, $C_{5-6}$-cycloalkyl, $C_{7-11}$-aralkyl, aryl;

$R^2$ denotes H, $C_{1-12}$-alkyl, $C_{5-6}$-cycloalkyl, $C_{7-18}$-aralkyl, aryl; preferably $C_{1-6}$-alkyl, $C_{5-6}$-cycloalkyl, $C_{7-11}$-aralkyl, aryl;

$R^{11}$ and $R^{12}$ independently of one another denote H, $C_{1-6}$-alkyl, optionally substituted by one or more halogens, or aryl, optionally substituted by one or more halogens or $C_{1-6}$-alkyl; preferably H, $C_{1-6}$-alkyl or aryl; in particular and L denotes a neutral ligand; preferably $L^1$, $L^2$, $L^3$ or $L^4$;

$R^9$ and $R^{10}$ independently of one another denote H, $C_{1-6}$-alkyl, optionally substituted by one or more halogens, or aryl, optionally substituted by one or more halogens or $C_{1-6}$-alkyl; preferably H, $C_{1-6}$-alkyl or aryl;

with the proviso that $R^1$ and $R^2$ cannot simultaneously represent methyl. Therefore in another aspect the invention relates to a compound of formula 2,

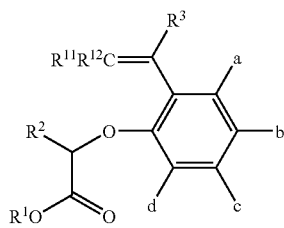

2 wherein $R^3$, a, b, c and d have the meanings given in claim 1; and $R^1$ denotes $C_{1-12}$-alkyl, $C_{5-6}$-cycloalkyl, $C_{7-18}$-aralkyl, aryl;

$R^2$ denotes H, $C_{1-12}$-alkyl, $C_{5-6}$-cycloalkyl, $C_{7-18}$-aralkyl, aryl;

$R^{11}$ and $R^{12}$ independently of one another denote H, $C_{1-6}$-alkyl, optionally substituted by one or more halogens, or aryl, optionally substituted by one or more halogens or $C_{1-6}$-alkyl;

with the proviso that $R^1$ and $R^2$ cannot simultaneously represent methyl. Preferred compounds are the compounds of formula 2, wherein $R^1$ denotes $C_{1-6}$-alkyl, $C_{5-6}$-cycloalkyl, $C_{7-11}$-aralkyl, aryl;

$R^2$ denotes H, $C_{1-6}$-alkyl, $C_{5-6}$-cycloalkyl, $C_{7-11}$-aralkyl, aryl;

$R^{11}$ and $R^{12}$ independently of one another denote H, $C_{1-4}$-alkyl, optionally substituted by one or more halogens, or aryl, optionally substituted by one or more halogens or methyl;

with the proviso that $R^1$ and $R^2$ cannot simultaneously represent methyl.

Particularly preferred are the compounds of formula 2 wherein $R^1$ denotes methyl, cyclohexyl, benzyl, phenyl;
$R^2$ denotes H, methyl, cyclohexyl, benzyl, phenyl;
$R^{11}$ denotes H;
$R^{12}$ denotes H or methyl;

with the proviso that $R^1$ and $R^2$ cannot simultaneously represent methyl.

The ligands and complexes shown may occur as pure enantiomers or pairs of enantiomers. Within the scope of the invention therefore the pure enantiomers to certain racemates may also be present, which may transfer the enantiomerism to a substrate through the stereocentre during the catalysis.

In an additional aspect the invention relates to a process for carrying out metathesis reactions, in which two compounds are reacted each of which contains an olefinic double bond or wherein one of the compounds contains at least two olefinic double bonds and wherein one of the above-mentioned compounds of formula 1 is used as catalyst, or a process for carrying out ring-closing metathesis (RCM) or cross metathesis (CM) which involves a compound which contains two olefinic double bonds as substrate and one of the compounds of formula 1 as catalyst.

Terms and Definitions Used

By "anionic ligands" (X or X') are meant, within the scope of the invention, negatively charged molecules or atoms with electron donor properties. Examples which may be mentioned here include halogens, such as fluorine, chlorine, bromine or iodine.

By "neutral ligands" (L) are meant, within the scope of the invention, uncharged or charge-neutral molecules or atoms with electron donor properties. Examples which may be mentioned here include tertiary phosphines which contain aliphatic, cycloaliphatic and aromatic hydrocarbon groups, such as trioctylphosphine, tridodecylphosphine, tricyclohexylphosphine, tris-(2-methylcyclohexyl)phosphine and tris-(o-tolyl)phosphine. Examples of particularly preferred neutral ligands include NHC ligands such as e.g. the compounds described by formulae $L^1$, $L^2$, $L^3$ and $L^4$:

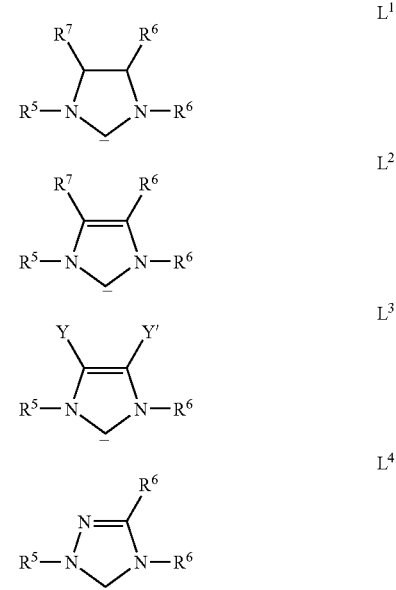

wherein
$R^5$ and $R^6$ independently of one another denote H, $C_{1-6}$-alkyl or aryl,
$R^7$ and $R^8$ independently of one another denote H, $C_{1-6}$-alkyl, $C_{1-6}$-alkenyl or aryl or together form a 3 or 4-membered alkylene bridge and
Y and Y' denote halogen.

By the term "$C_{1-12}$-alkyl" (including those which are part of other groups) are meant branched and unbranched alkyl groups with 1 to 12 carbon atoms, and accordingly by the term "$C_{1-6}$-alkyl" are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 6 carbon atoms are preferred while those with 1 to 4 carbon atoms are particularly preferred. Examples include: methyl, ethyl, n-propyl, iso-propyl, n-butyl, iso-butyl, sec-butyl, tert-butyl, n-pentyl, iso-pentyl, neo-pentyl or hexyl. In some cases the abbreviations Me, Et, n-Pr, i-Pr, n-Bu, i-Bu, t-Bu, etc. may be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl, etc.

By the term "$C_{2-12}$-alkenyl" (including those which are part of other groups) are meant branched and unbranched alkenyl groups with 2 to 12 carbon atoms, provided that they have at least one double bond. Accordingly, the term "$C_{2-6}$-alkenyl" denotes alkenyl groups with 2 to 6 carbon atoms and the term "$C_{2-4}$-alkenyl" denotes branched and unbranched alkenyl groups with 2 to 4 carbon atoms. Alkenyl groups with 2 to 6 carbon atoms are preferred, those with 2 to 4 carbon atoms are particularly preferred. Examples include: ethenyl or vinyl, propenyl, butenyl, pentenyl, or hexenyl. Unless otherwise specified, the definitions propenyl, butenyl, pentenyl and hexenyl include all possible isomeric forms of the groups in question. Thus for example propenyl includes 1-propenyl and 2-propenyl, butenyl includes 1,2- and 3-butenyl, 1-methyl-1-propenyl, 1-methyl-2-propenyl etc.

By the term "$C_{2-12}$-alkynyl" (including those which are part of other groups) are meant branched and unbranched alkynyl groups with 2 to 12 carbon atoms, provided that they have at least one triple bond. Accordingly, the term "$C_{2-6}$-alkynyl" refers to alkynyl groups with 2 to 6 carbon atoms and the term "$C_{2-4}$-alkynyl" refers to branched and unbranched alkynyl groups with 2 to 4 carbon atoms. Alkynyl groups with 2 to 6 carbon atoms are preferred, those with 2 to 4 carbon atoms are particularly preferred. The following are mentioned by way of example: ethynyl, propynyl, butynyl, pentynyl, or hexynyl. Unless otherwise specified, the definitions propynyl, butynyl, pentynyl and hexynyl include all possible isomeric forms of the groups in question. Thus for example propynyl includes 1-propynyl and 2-propynyl, butynyl includes 1,2- and 3-butynyl, 1-methyl-1-propynyl, 1-methyl-2-propynyl, etc.

By the term "$C_{1-12}$-alkoxy" (including those which are part of other groups) are meant branched and unbranched alkoxy groups with 1 to 12 carbon atoms, and similarly the term "$C_{1-6}$-alkoxy" denotes branched and unbranched alkoxy groups with 1 to 6 carbon atoms and the term "$C_{1-4}$-alkoxy" denotes branched and unbranched alkoxy groups with 1 to 4 carbon atoms. Alkoxy groups with 1 to 6 carbon atoms are preferred, those with 1 to 4 carbon atoms are particularly preferred. The following are mentioned by way of example: methoxy, ethoxy, propoxy, butoxy or pentoxy. The abbreviations MeO, EtO, PrO, etc. may also be used in some cases for the above-mentioned groups. Unless otherwise specified, the definitions propoxy, butoxy and pentoxy include all possible isomeric forms of the groups in question. Thus for example propoxy includes n-propoxy and iso-propoxy, butoxy includes iso-butoxy, sec-butoxy and tert-butoxy etc.

By the term "$C_{5-6}$-cycloalkyl" (including those which are part of other groups) are meant cyclic alkyl groups with 5 or 6 carbon atoms. The following are mentioned by way of example: cyclopentyl or cyclohexyl. Unless otherwise specified, the cyclic alkyl groups may be substituted by one or more groups selected from among methyl, ethyl, iso-propyl, tert-butyl, hydroxy, fluorine, chlorine, bromine and iodine.

By the term "aryl" (including those which are part of other groups) are meant aromatic ring systems with 6 or 10 carbon atoms. The following are mentioned by way of example: phenyl or naphthyl, the preferred aryl group being phenyl. Unless otherwise specified, the aromatic groups may be substituted by one or more groups selected from among methyl, ethyl, iso-propyl, tert-butyl, hydroxy, fluorine, chlorine, bromine and iodine.

By the term "$C_{7-18}$-aralkyl" (including those which are part of other groups) are meant branched and unbranched alkyl groups with 1 to 8 carbon atoms which are substituted by an aromatic ring system with 6 or 10 carbon atoms, and similarly the term "$C_{7-11}$-aralkyl" denotes branched and unbranched alkyl groups with 1 to 4 carbon atoms which are substituted by an aromatic ring system with 6 carbon atoms. The following are mentioned by way of example: benzyl, 1- or 2-phenylethyl. Unless otherwise specified, the aromatic groups may be substituted by one or more groups selected from among methyl, ethyl, iso-propyl, tert-butyl, hydroxy, fluorine, chlorine, bromine and iodine.

PREPARATION OF THE COMPOUNDS

The reaction of the ruthenium complexes of formula 3 with the preligands of formula 2 is carried out in inert solvents, e.g. $CH_2Cl_2$ at approx. 0° to 80° C. It is advantageous to add CuCl to the reaction mixture. The reactants are generally used in equivalent amounts, but in order to increase the yield the more valuable component in each case may be used in a smaller amount. It may also be useful to produce the complex of formula 3 in situ from other ruthenium compounds and ligand pre-products, e.g. dihydroimidazolinium salts, in order to arrive at the new metathesis catalysts of formula 1 with the desired ligand combination in each case, via the resulting complexes of formula 3.

The metathesis catalysts of formula 1 prepared by ligand exchange reaction may be separated off from other reaction products which are insoluble in the reaction mixture, by filtration of the solution thereof and, after concentration of the solution, are obtained in pure form by chromatography or crystallisation. However, it is also possible to use the crude products or the catalysts produced in situ directly to carry out metathesis reactions.

The preligands of formula 2 may be prepared in a manner known per se from aromatic aldehydes which contain corresponding substituents, by reactions of olefination, e.g. by reaction with phosphorylidene according to Wittig.

Particularly preferred is a new combined process which starts from optionally correspondingly substituted phenylallylethers, and leads by Claisen rearrangement and catalytic double bond isomerisation to optionally correspondingly substituted 2-alkenyl-phenols which are subsequently reacted by alkylation with α-halocarboxylic acid esters to obtain compounds of formula 2.

The alkylation of phenols to form alkyl-phenylethers is well known in the art and is usually carried out in a solvent in the presence of basic substances by reaction with nucleophilic reagents. The reaction with α-halocarboxylic acid esters proceeds particularly smoothly and with good yields. Suitable solvents include, for example, alcohols such as ethanol or aprotic polar solvents such as dimethylformamide. The alkylation may also be carried out under phase transfer conditions. Examples of basic substances include alkali metal carbonates, and similarly the alkali metal salts of the intermediate products which contain a free aromatically bound OH group may be used for this reaction.

In order to illustrate the sequence of synthesis which is preferably used to prepare compounds of formula 2, the preparation of (3-propenyl-biphen-2-yl) (1-methoxycarbonyl-ethyl)ether will now be described as a specific example:

Starting from 2-hydroxybiphenyl, 2-allyloxy-biphenyl is obtained by alkylation with allyl chloride in DMF as solvent in the presence of potassium carbonate. By thermal rearrangement at 190° C. in trichlorobenzene, 3-allyl-2-hydroxy-biphenyl is then obtained, which is catalytically rearranged (RhCl$_3$ H$_2$O) in ethanolic solution in the presence of p-toluenesulphonic acid to form an E/Z mixture of 3-propenyl-2-hydroxybiphenyl. Alkylation of this intermediate product with methyl 2-bromopropionate yields the preligand (3-propenyl-biphen-2-yl)(1-methoxycarbonyl-ethyl)ether.

The compounds of formula 1 are highly active metathesis catalysts which may also be successfully used for carrying out difficult metathesis reactions, including all types of reactions of this kind (RCM, CM, ROMP etc.).

EXAMPLE 1

Preparation of a Metathesis Catalyst of Formula 1a.

1.1) Preparation of the New Preligand of Formula 2a:

A mixture of 500 mg (3.72 mmol) of 2-propenylphenol (E/Z mixture), prepared by Claisen rearrangement of phenylallylether followed by double bond isomerisation, 1.02 g of potassium carbonate (0.74 mmol) and 745 mg of rac. methyl 2-bromopropionate (4.46 mmol) and 10 ml of dimethylformamide was stirred overnight at RT and then for 4 hours at 80° C. The reaction mixture was then added to 40 ml of water and extracted three times with 30 ml diethyl ether. The organic phase was washed with 5% sodium hydroxide solution, separated off, dried with Na$_2$SO$_4$ and concentrated by evaporation. 685 mg (83.6% of theory) of virtually pure methyl 2-(2-propenyl-phenyloxy)propionate were obtained.

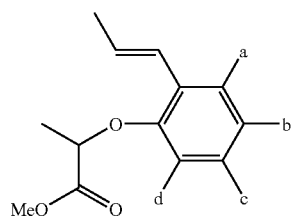

2a 1.2) Preparation of the Metathesis Catalyst of Formula 1a.

424 mg (0.5 mmol) of Grubb's catalyst, 2nd generation,

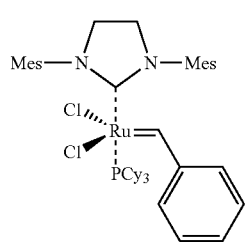

and 59 mg CuCl (0.6 mmol) were placed in a Schlenk tube, and under argon a solution of 134 mg (0.6 mmol) of methyl 2-(2-propenyl-phenyloxy)propionate, dissolved in 10 ml CH$_2$Cl$_2$, was added. The mixture was stirred for 1 hour at 40° C., then evaporated down i.v, the residue was taken up in 20 ml of ethyl acetate and the cloudy solution obtained was filtered. The crude product obtained after evaporation of the solvent was purified by chromatography carried out twice (Merck silica gel type 9385, 1st eluent AcOEt/cyclohexane 3:7, 2nd eluent AcOEt/cyclohexane 1:1). 193 mg (58% of theory) of pure product were obtained.

HRMS(EI): C$_{32}$H$_{38}$N$_2$O$_3$Cl$_2$Ru

Calculated: [M$^+$]670.13030, found: 670.13467

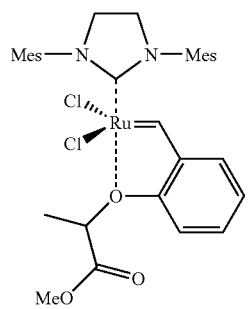

1a

EXAMPLE 2

Use of the catalyst of formula 1a prepared according to the invention and comparison of its activity with the known catalyst of formula A (see above).

2.1) Ring-Closing Metathesis (RCM) Using 1a:

A solution of 2.7 mg (0.004 mmol) of the catalyst 1a obtained according to Example 1 in 1 ml dichloromethane at 25° C. was added to a solution of 100 mg (0.4 mmol) diethyl allyl-methallyl-malonate (substrate) in 20 ml of dichloromethane. The reaction mixture was kept at this temperature for 2 hours. After this time a sample was taken, the catalyst was destroyed by the addition of ethylvinylether and the sample was analysed by gas chromatography (comparison with substrate and ring-closing product prepared in known manner). The level of conversion of the substrate into the metathesis product (1,1-bis-ethoxycarbonyl-3-methyl-cyclopent-3-ene) was 89%.

2.2) RCM Using the Known Catalyst of Formula A:

The same substrate was reacted as described in Example 2.1, but using 2.5 mol % of the known catalyst A. Investigation by gas chromatography showed that the level of conversion into the ring-closing product was 18%.

EXAMPLE 3

Use of the catalyst of formula 1a prepared according to the invention and comparison of its activity with the known catalyst of formula D (see above).

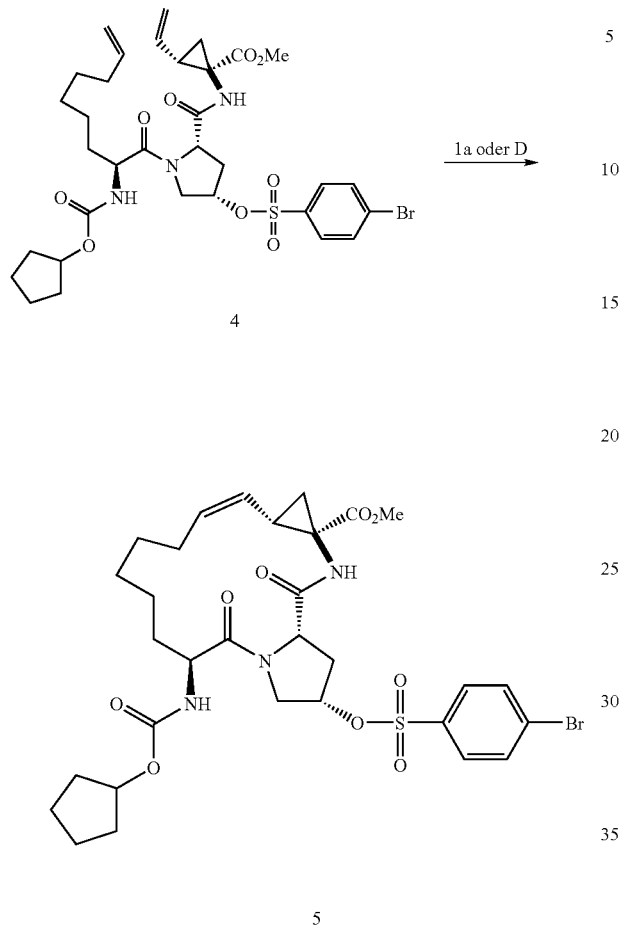

4

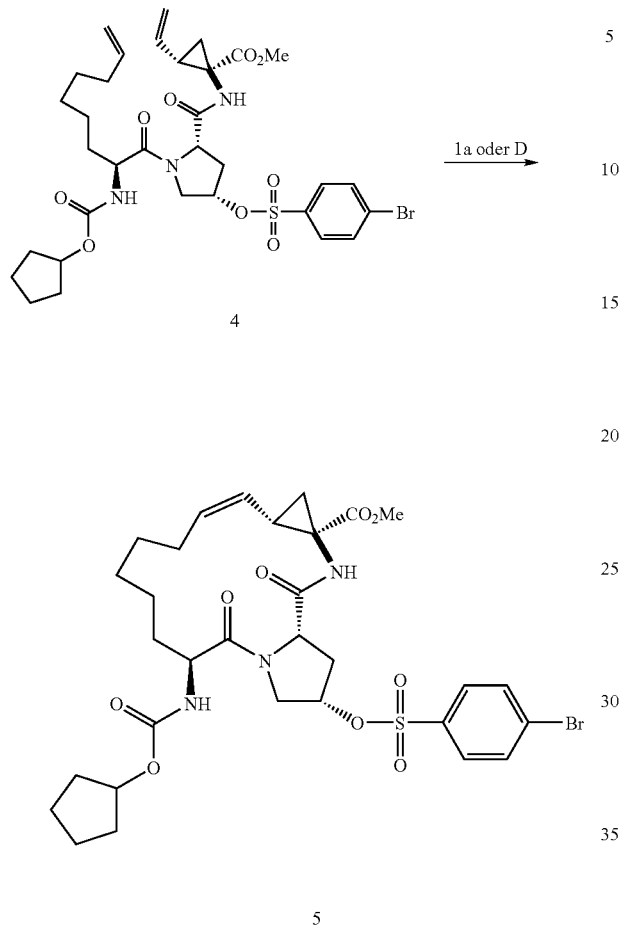

5

4 is dissolved in 10 ml of degassed toluene and heated to 80° C., freshly prepared catalyst is added under nitrogen ($1^{st}$) and the resulting mixture is stirred for 60 min at 80° C. The reaction is tested by HPLC and a further amount of the catalyst is added ($2^{nd}$). After another 60 min the reaction is tested once more by HPLC.

FIG. 1 shows the cyclisation rate of 4 (T=0 min:0.4 mol %; T=60 min:0.2 mol %). Table 1 shows the results of an HPLC analysis in which the results are compared with the known catalyst of formula D (*Angew. Chem. Int. Ed.* 2002, 41, 4038).

TABLE 1

| Catalyst | $1^{st}$ [mol %] $2^{nd}$ [mol %] | 4 [mol] | toluene [ml] | reaction [% peak at 200 nm] 5 [60 min] 5 [120 min] | 4 [60 min] 4 [120 min] |
|---|---|---|---|---|---|
| 1a | 0.4 | 0.0075 | 554 | 82.8 | |
|  | 0.2 |  |  | 94.6 | |
| D | 0.4 | 0.015 | 1008 | 77.4 | 22.6 |
|  | 0.2 |  |  | 92.8 | 7.2 |

What is claimed is:

1. A compound of formula 1, wherein

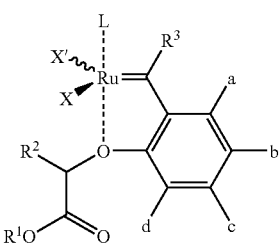

1

X and X' each denote halogen;
L denotes:
   a ligand of formula $L^1$, $L^2$, $L^3$ or $L^4$,

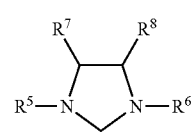

$L^1$

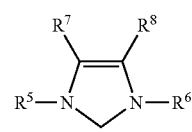

$L^2$

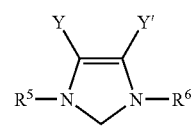

$L^3$

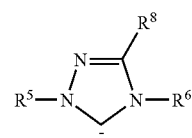

$L^4$ wherein
   $R^5$ and $R^6$ independently of one another denote H, $C_{1-6}$-alkyl or aryl;
   $R^7$ and $R^8$ independently of one another denote H, $C_{1-6}$-alkyl, $C_{2-6}$-alkenyl or aryl; or
   $R^7$ and $R^8$ together form a 3 or 4-membered alkylene bridge; and
   Y and Y' denote halogen;
a, b, c, d independently of one another denote H, -$NO_2$, $C_{1-12}$-alkyl, $C_{1-12}$-alkoxy or phenyl, wherein phenyl may optionally be substituted by a group selected from $C_{1-6}$-alkyl and $C_{1-6}$-alkoxy;
$R^1$ denotes $C_{1-12}$-alkyl, $C_{5-6}$-cycloalkyl, $C_{7-18}$-aralkyl or aryl;
$R^2$ denotes H, $C_{1-12}$-alkyl, $C_{5-6}$-cycloalkyl, $C_{7-18}$-aralkyl or aryl; and
$R^3$ denotes H, $C_{1-20}$-alkyl, $C_{2-20}$-alkenyl, $C_{2-20}$-alkynyl or aryl.

2. A compound of formula 1 according to claim 1, wherein a, b, c denote H; and d denotes phenyl substituted by a group selected from $C_{1-6}$-alkyl and $C_{1-6}$-alkoxy.

3. A compound of formula 1 according to claim 1, wherein a, c, d denote H; and b denotes -$NO_2$.

4. A compound of formula 1 according to claim 1, wherein L denotes a ligand of formula $L^1$, $L^2$, $L^3$ or $L^4$,

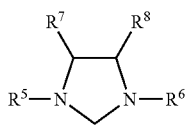

$L^1$

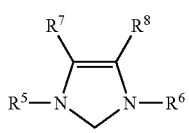

$L^2$

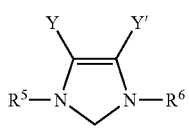

$L^3$

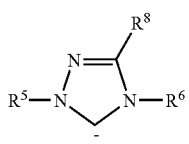

$L^4$ wherein $R^5$ and $R^6$ independently of one another denote H, $C_{1-6}$-alkyl or aryl;

$R^7$ and $R^8$ independently of one another denote H, $C_{1-6}$-alkyl, $C_{2-6}$-alkenyl or aryl; or $R^7$ and $R^8$ together form a 3 or 4-membered alkylene bridge; and Y and Y' denote halogen.

5. A compound of formula 1 according to claim 4, wherein

X and X' each denote Cl;

L denotes a ligand of formula $L^1$;

a, b, c, d denote H;

$R^1$ denotes methyl;

$R^2$ denotes methyl;

$R^3$ denotes H;

$R^5$ and $R^6$ denote mesityl; and $R^7$ and $R^8$ denote H.

6. A compound of formula 2:

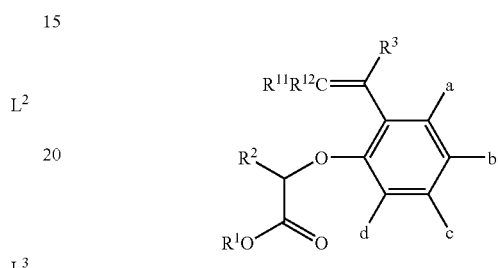

wherein:

$R^1$ denotes $C_{1-12}$-alkyl, $C_{5-6}$-cycloalkyl, $C_{7-18}$-aralkyl or aryl;

$R^2$ denotes H, $C_{1-12}$-alkyl, $C_{5-6}$-cycloalkyl, $C_{7-18}$-aralkyl or aryl;

$R^3$ denotes H, $C_{1-20}$-alkyl, $C_{2-20}$-alkenyl, $C_{2-20}$-alkynyl or aryl;

a, b, c, d independently of one another denote H, -$NO_2$, $C_{1-12}$-alkyl, $C_{1-12}$-alkoxy or phenyl, wherein phenyl may optionally be substituted by a group selected from $C_{1-6}$-alkyl and $C_{1-6}$-alkoxy;

$R^{11}$ and $R^{12}$ independently of one another denote H; $C_{1-6}$-alkyl optionally substituted by one or more halogens; or aryl optionally substituted by one or more halogens or $C_{1-6}$-alkyl;

with the proviso that $R^1$ and $R^2$ cannot simultaneously represent methyl.

* * * * *